United States Patent [19]
Owens et al.

[11] Patent Number: 6,090,569
[45] Date of Patent: Jul. 18, 2000

[54] SELECTION OF LIVESTOCK USING IGF LEVELS

[75] Inventors: Phillip Clyde Owens, Prospect; Roger Gregory Campbell; Brian Gerard Luxford, both of Corowa, all of Australia; Paul Edward Walton, Kansas City, Kans.

[73] Assignees: Bunge Meat Industries Ltd.; Pig Research and Development Corporation; Gropep PTY Ltd., all of Adelaide, South Africa

[21] Appl. No.: 08/945,774

[22] PCT Filed: May 2, 1996

[86] PCT No.: PCT/AU96/00252

§ 371 Date: Feb. 2, 1998

§ 102(e) Date: Feb. 2, 1998

[87] PCT Pub. No.: WO96/35127

PCT Pub. Date: Nov. 7, 1996

[30] Foreign Application Priority Data

May 2, 1995 [AU] Australia ............................... PN 2711

[51] Int. Cl.[7] .................................................. G01N 33/53
[52] U.S. Cl. ............................................ 435/7.92; 514/3
[58] Field of Search ................................. 514/3; 435/7.92

[56] References Cited

U.S. PATENT DOCUMENTS 5,187,151  2/1993  Clark et al. .................................. 514/3

OTHER PUBLICATIONS

Gluckman, P.D et al, Domestic Animal Endocrinology, vol. 5(3), pp. 209–217, 1988.
Donovan SM et al, Pediatric Research, vol. 36(2), pp. 159–168, 1994.
Lamberson, WR et al. Journal of Animal Science, vol. 73(11), pp. 3241–3245, 1995.
Owens, PC et al, Journal of Endocrinology, vol. 128, pp. 439–447, 1991.
Boge, A et al. Experimental and Clinical Endocrinology and Diabetes, vol. 103, pp. 99–104, 1995.
Speck, PA et al, Proc. Aust. Soc. Animal Prod. vol. 18, p. 551, 1990.
Daughday, WH et al, General and Comparative Endocrinology, vol. 59, pp. 316–325, 1985.
Lord, APD et al, Journal of Endocrinology, vol. 129, pp. 59–68, 1991.
Louveau, I et al, Reprod. Nutr. Dev., vol. 31, pp. 205–216, 1991.
Jones, EJ et al, J Animal Science, vol. 69(4), pp. 1607–1615, 1991.
Spicer, LJ et al, Livestock Production Science, vol. 33, pp. 355–360, 1993.
Latimer, AM et al, Endocrinology, vol. 133(3), pp. 1312–1319, 1993.
Koistinen, Hannu et al, Clinical Chemistry, vol. 40(4), pp. 531–536, 1994.
Gerrard, DE et al, Domestic Animal Endocrinology, vol. 11(4), pp. 339–347, 1994.
Park, NH et al, Journal Animal Science, vol. 70(suppl. 1), p. 203, abstract 264, 1992.
Chard, T, Growth Regulation, vol. 4(3), pp. 91–100, 1994.
Becker, BA et al, Journal of Animal Science, vol. 71, pp. 2375–2387, 1993.
Gluckman, P. D. Et al, "Relationships between plasma concentrations of placental lactogen, Insulin–Like Growth Factors, metabolites and lamb size in late gestation ewes subject to nutritional supplementations and in their lambs at birth." Domestic Animal Endrocinology, vol. 5, No. 3, (Jan. 1988) pp. 209–217. See especially page 212 Para 1, p 214 para 3.
Sterle, J. A. Et al, "Effects of Recombinant Porcine Somatotrophin on Placental Size, Fetal Growth, and IGF–I and IGF–II Concentrations in Pigs." Journal of Animal Science, vol. 73, No. 10, (1995), pp. 2980–2985. See especially p. 2984 col. 2.
Schwarz, F. J. et al "Effects of sex and growth on plasma concentrations of growth hormone, insulin–like growth factor–I and insulin in fattening simmental cattle." Journal of Animal Physiology and Animal Nutrition, vol. 68, No. 4–5, (1992) pp. 263–271.
Herrler, A. et al "Effects of Insulin–like Growth Factor–I on In–vitro Production of Bovine Embroyos." Theriogenology: an international journal of animal reproduction, vol. 37, No. 6 (1992) pp. 1213–1224 especially p. 1220.
Hannon, K. et al "Relationship of Liver and Skeletal Muscle IGF–I mRNA to Plasma GH Profile Production of IGF–I by Liver, Plasma IGF–I concentrations, and Growth Rates of Cattle." Proceedings of the Society for Experimental Biology and Medicine, vol. 196, No. 2, (1991), pp. 155–163, see Tables II and III.
Taylor, J. A. Et al, "Serum concentrations of insulin–like growth factor I and cholesterol in relation to protein and fat deposition in growing pigs." Animal Production, vol. 55, No. 2, (1992) pp. 257–264, see p. 259.
Bishop, M. D. Et al, "The relationship of insulin–like growth factor–I with postweaning performance in angus beef cattle." Journal of Animal Science, vol. 67, No. 11, (1989) pp. 2872–2880.
Echternkamp, S. E. Et al, "Concentrations of insulin–like growth factor–I in blood and ovarian follicular fluid of cattle selected for twins." Biology of Reproduction, vol. 43, No. 1, (1990), pp. 8–14.
Coleman, M. E. Et al, "Porcine somatotrophin increases IGF–I mRNA abundance in liver and subcutaneous adipose tissue but not in skeletal muscle of growing pigs." Journal of Animal Science, vol. 72, No. 4, (1994), pp. 918–924.
Jones, J. I. Et al, "Insulin–like Growth Factors and Their Binding Proteins: Biological Actions." Endocrine Reviews, vol. 16, No. 1, (1995) pp. 3–34.
Lowe, W. L. "Insulin–like Growth Factors." Scientific American: Science & Medicine, vol. 3, No. 2, (Mar.–Apr. 1996), pp. 62–71.

*Primary Examiner*—James C. Housel
*Assistant Examiner*—Ginny Allen Portner
*Attorney, Agent, or Firm*—Ladas & Parry

[57] ABSTRACT

The present invention provides methods of producing animals that have higher than average carcass quality, higher than average feed conversion efficiency, higher than average growth rate, lower than average voluntary feed intake and/or higher than average reproductive capacity.

5 Claims, No Drawings

SELECTION OF LIVESTOCK USING IGF LEVELS

This Application is a National Stage Application of PCT/AU96/00252, filed May 2, 1996, which claims priority to Australian Application, PN 2711, filed May 2, 1995.

This invention relates to animal husbandry, and in particular to a method of producing animals that have higher than average carcass quality, higher than average feed conversion efficiency, higher than average growth rate, lower than average voluntary feed intake and/or higher than average reproductive capacity.

The quality of meat products is an important factor in consumer choice. The desirability to the consumer of a particular type of meat depends upon such parameters as price, tenderness and appearance.

Nutritional factors, including the perceived health benefits of the meat, are an increasingly important influence in this area, and among these a high carcass quality (ratio of lean meat to fat) is important. A high ratio of lean meat to fat is also advantageous in the processing of meat, since extensive trimming of fat and disposal of fat is avoided. In addition, a high ratio of lean meat to fat is advantageous for the efficiency of growth and cost of production, in that typically greater than four times the amount of feed is required to deposit 1 kg of fat compared to that necessary to deposit 1 kg of lean tissue.

Feed conversion efficiency, growth rate, voluntary feed intake and reproductive capacity are important economical considerations for those involved in animal husbandry.

It is known to improve growth rate and carcass quality by selective breeding. The process of selective breeding relies on the fact that within any population of individuals, variation will exist for any particular character. Part of this variation will be caused by the individuals possessing different genes. Selective breeding aims to continually improve the average performance of a population by increasing the frequency of the favourable genes in the next generation by selecting as parents individuals which possess these genes. In the most part the individual genes themselves cannot be identified, so selection is based on the relative performance of the animals for the characteristics which are of interest such as growth rate, carcass quality, feed conversion efficiency, voluntary feed intake and reproductive capacity.

Inclusion of a performance trait into a genetic selection program depends on the following factors:
1. Relative economic merit of improvement of each trait.
2. The proportion of the variation (or the superiority of the parents) which can be attributed to the animals' genes. This is known as the heritability of the trait. The higher the heritability the greater the selection response.
3. The cost of measuring the trait.
4. The age at which the trait can be measured.
5. The effect that selection response in one trait has on the magnitude of other traits. This el-ect is quantified as the genetic correlation between any two traits. Genetic correlations occur because genes can affect more than one trait either favourably or adversely.

In the prior art genetic selection has been shown to be effective in improving numerous traits including growth rate and carcass quality. Typically animals are selected for improved growth rate and/or carcass as young adults. In the case of pigs, such selection occurs at around six months of age and is based on physical measurements of, for example, P2 fat thickness or backfat.

However, selection suffers from several problems, including disadvantages associated with having to use entire male animals in selection programmes. For example, in the majority of pig producing countries male pigs are castrated between two and four weeks of age to prevent boar taint. Boar taint refers to the presence of off-odours and off-flavours found in the meat of some entire male pigs. At the usual slaughter age of 6 months, the value of an entire male pig is up to 50% less than a castrate in countries where castration is practiced. Therefore, as only less than 5% of entire males are selected for breeding in a typical example, there is a substantial cost in not castrating the other 95% to enable the appropriate measurements to be taken at around 6 months.

Apart from the disadvantages associated with raring to use entire male animals in generic selection programmes the selection of animals for improved growth performance and improved carcass quality (higher lean:fat ratio) is inherently expensive because of the large numbers of animals involved and the need to use expensive equipment, facilities and labour to obtain the appropriate measurements.

In addition the measures of growth performance and carcass quality generally made in genetic selection programmes are based on indirect rather than direct measures of the intrinsic or biological mechanisms determining growth performance or the lean:fat ratio of the carcass. Furthermore, because of the cost involved one of the most accurate indicators of the protein or muscle growth capacity of pigs and other animal species namely the feed:gain ratio is rarely measured in selection programmes for mammalian species. All of these factors make genetic improvement a costly but at the same time inaccurate or compromised technology.

It is an object of the present invention to overcome or at least alleviate, one or more of the difficulties related to the prior art.

In a first aspect of the present invention, there is provided a method for identifying animals that are subsequently likely to produce offspring with higher than average carcass quality, better than average feed conversion efficiency, higher than average growth rate, lower than average voluntary feed intake and/or higher than average reproductive capacity, which method includes determining the concentration of IGF-I, IGF-II or IGFBP-3 in a biological sample from said animals and selecting for breeding those animals in which said concentration is lower than average.

In a second aspect, the present invention provides a method for producing animals having higher than average carcass quality, better than average feed conversion efficiency, higher than average growth rate, lower than average voluntary feed intake and/or higher than average reproductive capacity, which method includes determining the concentration of IGF-I, IGF-II or IGFBP-3 therefor in a biological sample from animals and breeding from those animals in which said concentration is lower than average.

In a third aspect the present invention provides an animal whenever bred by the abovementioned method.

The present invention allows much more rapid and genuine improvements in, inter alia, growth performance, carcass quality and overall productivity because selection is based on more direct measures or biological indicators of muscle growth capacity. This is the single biggest factor determining growth performance and carcass quality. Additionally the cost of selection is reduced because the present invention allows animals to be screened for their genetic potential early in life near the time castration would normally be performed, rather than at the end of the "productive" or commercial life.

The methods of the present invention involve determining the concentration of a growth factor and/or binding protein therefor.

The concentration of IGF-I, IGF-II or IGFBP-3 therefor may be measured by directly measuring the protein concentration or by indirectly measuring the protein concentration, for example by measuring the level of mRNA for IGF-I, IGF-II or IGFBP-3 or by measuring differences in the DNA encoding IGF-I, IGF-II or IGFBP-3 (see below).

The concentration of IGF-I, IGF-II or IGFBP-3 therefor is measured in a biological sample preferably obtained from prepubertal animals.

The choice of the actual prepubertal age selected for the concentration measurement will differ between species as a result of their different rates of growth. In the case of mammalian species, the nutritional dependency of the young mammal upon maternal milk supply ceases at the age of weaning. For this reason the concentration measurement is preferably carried out between weaning and puberty. Measurements are more preferably carried out near weaning than near puberty because the cost of maintaining animals before the selection period is reduced.

The concentration of IGF-I, IGF-II or IGFBP-3 therefor may be measured in any suitable biological sample from the animal. If the concentration is measured directly, preferably the biological sample is blood or other biological fluids, and/or extracts thereof from the animal. Preferably the con-entration of IGF-I, IGF-II or IGFBP-3 is measured in the blood, more preferable the serum, most preferably the plasma to the animals. If the concentration IGF-I, IGF-II or IGFBP-3 therefor is measured indirectly, preferably the biological sample is a tissue sample.

The concentration of IGF-I, IGF-II or IGFBP-3 may be measured directly by any suitable assay, for example radioimmunoassay, immunoradiometric assay, enzyme-linked immunosorbent assay, as well as other immunochemical assays. A radioimmunoassay (RIA) has been found to be particularly suitable. For measurement of IGF-I, IGFBP-blocked IGF-I RIA is preferred. For measurement of IGF-II, IGFBP-blocked IGF-II RIA is preferred.

There is a large body of literature that shows that the proteins IGF-I, IGF-II and IGFBP-3 are not stored within tissues before they are secreted into blood and/or other body fluids, and that their rates of secretion from their sites of biosynthesis are proportional to their rates of intracellular synthesis by tissues, and also that their concentrations in biological fluids are related to their rates of intracellular synthesis within tissues. Their rates of biosynthesis are determined primarily by the concentration or abundance within tissues and/or cells of their messenger ribonucleic acids (mRNA). Therefore, measurement of IGF-I mRNA, IGF-II mRNA and/or IGFBP-3 mRNA within biological tissues or cells, for example by hybridisation, Northern hybridisation, ribonuclease protection assay or reverse-transcriptase polymerase chain reaction methods, may be used instead of measurements of IGF-I protein, IGF-II protein or IGFBP-3 protein in biological fluids.

It is known that changes in gene structure, specifically differences in the sequence of deoxyribonucleic acid (DNA) bases within genes, alters the rate of synthesis of the protein products of genes. These changes are known to occur by mutation causing heritable differences in the structure of a particular gene between individual animals of the same species. These differences are known as allelic variations in gene structure. Therefore, measurement of the difference in DNA base sequences of the IGF-I gene, the IGF-II gene or the IGFBP-3 gene in biological tissues or cells, for example by hybridisation, Southern hybridisation, restriction fragment length polymorphism analysis, polymerase chain reaction, or reverse-transcriptase polymerase chain reaction methods, may also be used instead of measurements of IGF-I protein, IGF-II protein of IGFBP-3 protein in biological fluids.

In prepubertal pigs, for example a population in which the average concentration of IGF-I In blood plasma is approximately 50 $\mu$g/l, a lower than average IGF-I concentration may be from approximately 5 $\mu$g/l or less to approximately 49 $\mu$g/l. More preferably, a lower than average IGF-I concentration in prepubertal pigs may be from approximately 5 $\mu$g/l to approximately 45 $\mu$g/l, most preferably from approximately 5 $\mu$g/l to approximately 30 $\mu$g/l. In a similar population in which the average concentration of IGF-II in blood plasma is approximately 225 $\mu$g/l, a lower than average IGF-II concentration may be from approximately 50 $\mu$g/l or less to approximately 200 $\mu$g/l. More preferably, a lower than average IGF-II concentration in prepubertal pigs may be from approximately 50 $\mu$g/l to approximately 175 $\mu$g/l, most preferably from approximately 50 $\mu$g/l to approximately 125 $\mu$g/l. In a similar population in which the average concentration of IGFBP-3 in blood plasma is approximately 575 $\mu$g/l, a lower than average IGFBP-3 concentration may be from approximately 50 $\mu$g/l or less to approximately 570 $\mu$g/l. More preferably, a lower than average IGFBP-3 concentration in prepubertal pigs may be from approximately 50 $\mu$g/l to approximately 550 $\mu$g/l, most preferably from approximately 50 $\mu$g/l to approximately 250 $\mu$g/l.

Alternatively, the methods of the present invention as it applies to pigs may include selecting for breeding or breeding from the approximately 10%, more preferably the approximately 5%, most preferably the approximately 1% of boars having the lowest concentration of IGF-I, IGF-II or IGFBP-3 therefor. In addition, the methods of the present invention may include selecting for breeding or breeding from the approximately 30%, more preferably the approximately 20%, most preferably the approximately 10% of gilts having the lowest concentration of growth factor and/or binding protein therefor.

The higher than average carcass quality may be a lower carcass fatness, or a higher ratio of lean meat to fat. Carcass quality in pigs may be measured by the amount of lean in the right hind leg at 23 weeks of age expressed as 2 percentage of the weight of the limb (LEAN). Alternatively, carcass quality may be measured by the depth of the backfat at 23 weeks of age (P2).

The higher than average carcass quality may be an improved carcass quality in the population of animals. Thus, regardless of the numerical values of the average LEAN and average P2 in a population of pigs, the methods of the present invention may increase LEAN by between approximately 0.01% and approximately 0.70% and/or reduce P2 by between approximately 0.01 mm and approximately 1 mm in the next generation of animals.

The better than average feed conversion efficiency may be a reduced rate of ingestion of food per unit of liveweight gained over time. This may be measured as the ratio of the average daily weight of feed consumed to the average dairy gain in liveweight between 18 and 23 weeks of age (DFE).

The better than average feed conversion efficiency may be an improved feed conversion efficiency in the population of animals. Thus, regardless of the numerical value of the average DFE in a population of pigs, the methods of the present invention may improve DFE, in other words reduce the feed/gain ratio, by between approximately 0.01 units and approximately 0.3 units in the next generation of animals.

A higher than average growth rate may be a higher than average daily growth rate. This may be measured in pigs by the average daily rate of live eight gain from birth to 23 weeks of age (ADG).

The higher than average growth rate may be an increased growth rate in the population of animals. Thus, regardless of the numerical value of the average ADG in a population of pigs, the methods of, the present invention may increase ADG by between approximately 1 g/d and approximately 25 g/d in the next generation of animals.

The lower than average voluntary feed intake may be a lower than average finisher average daily feed intake. This may be measured in pigs by the average weight of feed consumed daily between 18 and 23 weeks of age (DFI).

The lower than average voluntary feed intake may be a reduced voluntary feed intake in the population of animals. Thus, regardless of the numerical value of the average DFI in a population of pigs, the methods of the present invention may reduce DFI by between approximately 1 g/d and approximately 100 g/d in the next generation of animals.

The higher than average reproductive capacity may be measured as a higher than average number of animals born alive from the first pregnancy ($NBA_1$).

The higher than average reproductive capacity may be an increased reproductive capacity in the population of animals. Thus, regardless of the numerical value of the $NBA_1$ in a population of pigs, the methods of the present invention may increase $NBA_1$ by between approximately 0.01 and approximately 0.25 pigs per litter in the next generation of animals.

Although the present invention is particularly applicable to pigs, it is also applicable to other domestic species including horses, sheep, cattle, goats, deers, rabbits or birds such as ducks, geese and turkeys, chickens such as broiler chickens and layer chickens, and fish. Those skilled in the art can readily understand the applicability of the methods of the invention for genetic selection in species of animals other than pigs. More particularly, with the results demonstrated here for pigs, which are the opposite of expectations based on the prior art, it is a straightforward matter for those skilled in the art to apply the methods of the present invention to other species.

The methods of the present invention may be repeated over a number of subsequent generations of animals. Thus, the methods of the present invention may be applied to the progeny of those animals that were selected for breeding or bred from according to the methods of the present invention. The methods may be repeated over, for example, approximately 5 to approximately 10 generations.

In a population of pigs whose average LEAN is, for example, approximately 57%, and/or whose average P2 is, for example, approximately 13 mm, a higher than average carcass quality after approximately 5 to approximately 10 generations may be represented by a LEAN of approximately 58% to approximately 65% or more and/or a P2 of approximately 7 mm or less to approximately 12 mm. More preferably a higher than average carcass quality may be represented by a LEAN of approximately 60% to approximately 65% and/or by a P2 of approximately 7 mm to approximately 10 mm.

In a population of pigs whose average DFE is, for example, approximately 2.7, a higher than average feed conversion efficiency after approximately 5 to approximately 10 generations may be represented by a DFE of approximately 1.8 or less to approximately 2.6. More preferably, a better than average feed conversion efficiency may be represented by a DFE of approximately 1.8 to approximately 2.5.

In a population of pigs whose average ADG is, for example, approximately 625 g/day, a higher than average growth rate after approximately 5 to approximately 10 generations may be represented by an ADG of approximately 630 g/day to approximately 750 g/day or more. More preferably, a higher than average growth rate in pigs may be represented by an ADG of approximately 650 g/day to approximately 750 g/day.

In a population of pigs whose average DFI is, for example, approximately 2.6 kg/day, a lower than average voluntary feed intake after approximately 5 to approximately 10 generations may be represented by a DFI of approximately 1.8 kg/day or less to approximately 2.5 kg/day. More preferably, a lower than average voluntary feed intake may be represented by a DFI of approximately 1.8 kg/day to approximately 2.3 kg/day.

In a population of pigs whose average $NBA_1$ is, for example, approximately 9.5, a higher than average reproductive capacity after approximately 5 to approximately 10 generations may be represented by a $NBA_1$ of approximately 10 to approximately 15 or more. More preferably, a higher than average reproductive capacity may be represented by a $NBA_1$ of approximately 12 to approximately 15.

The present invention provides an improved means of producing animals that have higher than average growth performance, better than average feed conversion efficiency, lower than average voluntary feed intake, higher than average reproductive capacity and higher than average carcass quality than those methods known in the art.

The invention enables animals to be screened for, inter alia, their subsequent breeding value at, for example, only five weeks of age and/or enables genetic selection against carcass fatness (higher lean-fat ratio) to be made at the same time. This has a major advantage in that it enables animals to be screened in early life which in turn reduces overall selection costs by reducing the number of animals which have to be tested through to "normal" weights or ages (eg. approximately 110 kg or 26 weeks for pigs).

The invention is based on the surprising finding that animals with a lower than average concentration of IGF-I, IGF-II or IGFBP-3 therefor are more likely to produce progeny that have higher than average carcass quality, better than average feed conversion efficiency, higher than average growth rate, lower than average voluntary feed intake and/or higher than average reproductive capacity. More specifically, applicants have found that there is a window early in life, preferably at around 5 weeks in the case of pigs, which allows an animal's subsequent growth rate to be predicted from blood levels of IGF-I, IGF-II and/or IGFBP-3. Applicants have also surprisingly found that the concentrations of insulin-like growth factors and insulin-like growth factor-binding protein-3 in blood of prepubertal animals are genetically positively correlated with the feed conversion efficiency (measured as the ratio of feed consumed per unit gain in liveweight, the feed/gain), feed intake and with the carcass fatness of mature animals. In pigs, for example, blood plasma concentrations of IGF-I, IGF-II and/or IGFBP-3 at five weeks of age are genetically positively correlated with feed conversion efficiency (feed/gain) measured between eighteen and twenty-three weeks of age. Blood plasma concentrations of IGF-I, IGF-II and/or IGFBP-3 at five weeks of age are also genetically positively correlated with feed intake. Also, blood plasma concentrations of IGF-I and/or IGFBP-3 at five weeks of age are genetically positively correlated with carcass fatness at twenty-three weeks of age in pigs. In other words, the higher the IGF-I, IGF-II and/or IGFBP-3 concentration in blood of prepubertal animals, the fatter their offspring will be, the more feed they will consume, and the more feed they will consume per unit of liveweight gain. This goes against conventional wisdom that IGF-I is an anabolic agent such that pigs with IGF-I levels should be leaner. Applicants have also surprisingly found that there is a negative genetic correlation between the concentration of IGF-I, IGF-II and/or IGFBP-3 in blood of prepubertal animals and number born alive in first pregnancy of their progeny. These results indicate that genetic selection to reduce IGF-I, IGF-II and/or IGFBP-3 will have favourable consequences for the number of animals born alive in first pregnancy.

Genetic selection for high and for low concentrations of IGF-I in blood plasma of mice has been shown to produce differences in growth rate (rate of gain of liveweight) and mature body size and weight (Blair, McCutcheon, Mackenzie, Ormsby, Siddiqui, Breler & Gluckman, 1988, Endocrinology 123:1690–1691). After seven generations of selective breeding, mice of the high IGF-I line were significantly heavier than those of the low IGF-I line (Blair et al, 1988). However, genetic selection for and against IGF-I in mice did not affect the body composition of water, protein or fat (Siddiqui, Blair, McCutcheon, Mackenzie, Gluckman & Breier, 1990, Journal of Endocrinology 124:151–158). Also, genetic selection for and against IGF-I in mice did not alter responsiveness to testosterone, a natural hormone that is known to promote growth of muscle, to increase body protein composition, and to reduce the body content of fat in mice, pigs and other animal species (Siddiqui, McCutcheon, Mackenzie, Blair, Ormsby, Gluckman & Breier, 1989, Acta Endocrinologica [Copenhagen] 121:686–690).

The positive sign of the genetic correlation between IGF-I and carcass fat (P2 backfat) found by the applicants is the opposite of logical predictions based on understanding the prior art because administration of IGF-I to laboratory animals promotes growth of their lean tissues and reduces their body fat.

Genetic correlations between IGF-I and feed efficiency, expressed here as weight of feed consumed divided by live weight gained, have not been previously reported. The positive sign of this genetic correlation is the opposite of that expected from understanding the prior art because administration of IGF-I to animals has been reported to reduce their feed/gain ratio (Tomas F M, Knowles S E, Chandler C S, Francis G L, Owens P C &, Ballard F J [1993] Anabolic effects of insulin-like growth factor-I [IGF-I] and an IGF-I variant in normal female rats, Journal of Endocrinology, 137, 413–421)

Genetic correlations between IGFBP-3 and other biological traits haste not been reported previously.

The present invention will now be more fully described with reference to the accompanying examples. It should be understood however, that the description following is illustrative only and should not be taken in any way as a restriction on the generality of the invention described above.

EXAMPLE 1

Experimental Design

This experiment was performed with pigs. Thirty-six sires from one of two breedlines were mated with a total of 258 dams and the following traits were measured in approximately 970 of their offspring; finisher backfat (carcass P2 when slaughtered at 25 weeks of age), IGF-I at 5 weeks of age, and IGFBP-3 at 5 weeks of age.

Extracts of plasma for measurement of IGF-I were prepared by the acid-ethanol cryoprecipitation procedure as described by Breier, Gallaher and Gluckman in 1991 (Journal of Endocrinology 128, 347–357) except that the cryoprecipitation step was performed before pH neutralisation of the extract. The IGF-I content of these extracts was measured by a modification of the IGFBP-blocked RIA procedure, using excess IGF-II as the blocking agent, described for human blood plasma and human blood serum by Blum and Breier in 1994 in Growth Regulation 4 (supplement 1), 11–19. The modification employed is similar in principle to that described by Bang, Erikkson, Sara, Wivall and Hall in 1991 in Acta Endocrinologica 124, 620–629. Whereas Bang et al (1991) used radioiodinated des(1-3)IGF-I as radioligand, radioiodinated LR$^3$IGF-I was used as radioligand for IGF-I RIA in this example. The method used was validated for plasma from 5 week old pigs by comparison of the results with those obtained using conventional IGF-I RIA combined with size exclusion high performance liquid chromatography under acidic conditions (Owens, Johnson, Campbell & Ballard 1990, Journal of Endocrinology 124, 681–687). IGF-binding protein-3 (IGFBP-3) was measured by RIA according to the procedure published by Walton and Etherton in 1989 (Journal of Endocrinology 120.153–160) except that the porcine IGFBP-3 radioligand was prepared as described for radiolabelled human IGFBP-3 by Martin and Baxter in 1986 (Journal of Biological Chemistry 261–8754–8760).

The heritability and genetic correlations were estimated using a standard sib analysis. An explanation of the theoretical principles of this analysis are as described in "Introduction to Quantitative Genetics" (Falconer, D. S. (1981) Introduction to Quantitative Genetics (2nd Edition), Longman, London), the entire disclosure of which is incorporated herein by reference. The software used for the computer assisted analysis was LSMLMW which is a mixed model least squares and maximum likelihood program. The model used contains two sets of nested noninteracting random effects. The second set of nested random effects are nested within the first set of nested random effects and these are nested within a set of fixed effects.

$$Y_y klm = u + L_f + S_y + d_y k + Sex + e_y klm$$

where $L_f$=line (Two lines/breeds of pigs were used)

$S_y$=sire $d_y$k=dam

Sex=gender (Both male and female progeny were used)

This method allows the analysis to be carried out within line which effectively removes any between-line differences. The effect of sex/gender is also removed by treating it as a fixed effect in the model. P2 was standardised to a common weight.

Results

Table 1 summarises the number of observations. Tables 2 and 3 summarise the genetic analyses. Table 4 summarises the phenotypic associations.

TABLE 1

| Number of observations for different traits | | | | |
|---|---|---|---|---|
| TRAIT | IGF-I | IGFBP-3 | 5 wk wt | Backfat (P2) |
| N | 947 | 952 | 319 | 674 |

TABLE 2

Heritabilities of the measured traits

| TRAIT | HERITABILITY* |
|---|---|
| IGF-I | 0.10 ± 0.07 |
| IGFBP-3 | 0.15 ± 0.08 |
| Wt at 5 wk | 0.56 ± 0.20 |
| Backfat (P2) | 0.26 ± 0.13 |

*The standard error of the heritability estimate is also given.

The heritability measure of the backfat measurement falls within the range of published estimates. There have been a few estimates published for heritability of IGF-I in mice which are similar to the value recorded here. The mean heritability of IGF-I in mice has been estimated to be 0.15 and the standard error of this estimate is reported to be 0.12 (Blair, McCutcheon, Mackenzie, Gluckman, Ormsby & Breier, 1989, Genetics Research Cambridge 53:187–191). To our knowledge there have been no estimates of the heritability of IGF-binding proteins in any species.

TABLE 3

Genetic Correlations

|  | IGFBP-3* | Wt 5 wk* | P2* |
|---|---|---|---|
| IGF-I | 0.87 ± 0.16 | 0.96 ± 0.14 | 1.79 ± 0.50 |
| IGFBP-3 |  | 0.85 ± 0.15 | 0.97 ± 0.22 |
| Wt at 5 wk |  |  | 0.19 ± 0.99 |

*The standard error of each estimate is also given

TABLE 4

Phenotypic Correlations

|  | IGFBP-3* | Wt 5 wk* | P2* |
|---|---|---|---|
| IGF-1 | 0.48 | 0.29 | 0.15 |
|  | (p < 0.001) | (p < 0.001) | (p < 0.001) |
| IGFBP-3 |  | 0.38 | 0.11 |
|  |  | (p < 0.001) | (p < 0.001) |
| Wt at 5 wk |  |  | (p < 0.001) |

IGF-I, IGFBP-3 and weight at 5 weeks are highly correlated genetically with each other (Table 3) which is similar to the phenotypic correlations found in this study (Table 4).

From a genetic selection viewpoint, the most valuable estimates are the genetic correlations (Table 3). Of these, the most interesting is the high genetic correlation between IGF-I and/or IGFBP-3 concentration, and P2 fat thickness at 25 weeks. Plasma IGF-I and IGFBP-3 at 5 weeks of age were found to be stronger than weight at 5 weeks of age as genetic correlates of P2 backfat at 25 weeks of age. Of greater interest is the finding that the genetic correlations between IGF-I or IGFBP-3 and backfat (Table 3) were stronger than the phenotypic correlations (Table 4) between these traits.

Significant phenotypic correlations were also observed (Table 4), in particular the associations between IGF-I and/or IGFBP-3 concentration and weight at 5 weeks and depth of backfat at 25 weeks of age.

This example shows that IGF-I and/or IGFBP-3 and finisher backfat are genetically correlated in pigs. Unexpectedly however, the relationship is positive rather than negative as would have been assumed based on the anabolic actions of IGF-I (Thomas et at., 1993).

EXAMPLE 2

Experimental Design

This experiment was performed with pigs. A total of 165 sires from one of three breedlines were mated with a total of 1,388 dams of known parity (ie. whether this was their first, second, third or fourth pregnancy) from one of three breedlines. The following traits were measured in a total of between 1,542 and 4,670 of their offspring and in 13,015 litters born to females to whom they are genetically related: the number of animals born alive from each of the first three pregnancies ($NBA_1$, $NBA_2$ and $NBA_3$), the liveweight at approximately three weeks of age (ANW21) and the exact age in days at which this was measured, the average daily growth rate (average daily rate of liveweight gain or average daily gain from birth to twenty-three weeks of age (ADG)), the finisher average daily feed intake (DFI, average weight of feed consumed daily between eighteen and twenty-three weeks of age), the finisher average daily feed efficiency (DFE, ratio of the average daily weight of feed consumed to the average daily gain in liveweight between eighteen and twenty-three weeks of age), the amount of lean (non-fat) in the right hind leg at twenty-three weeks of age, expressed as a percentage of the weight of the limb (LEAN), the depth of backfat at twenty-three weeks of age (P2), and the concentration in blood plasma collected at five weeks of age of IGF-I, IGF-II and IGFBP-3.

IGF-I and IGFBP-3 were measured as described in Example 1. IGF-II was measured by a similar procedure to that used to measure IGF-I. Extracts of blood plasma for IGF-II measurement were prepared as described for measurement of IGF-I in Example 1. The IGF-II content of these extracts was measured by an IGFBP-blocked RIA procedure, adapted from that described for IGF-I assay of human blood plasma and human blood serum by Blum and Breier in 1994 cited in Example 1, except that IGF-I reagents were replaced by IGF-II reagents and vice versa as appropriate. Radioiodinated des(1-6)IGF-II was used as the radioligand in the IGF-II RIA. The method used to measure IGF-II was validated for blood plasma for five week old pigs by comparison of the results with those obtained using conventional IGF-II RIA combined with size exclusion high performance liquid chromatography of plasma under acidic conditions (Carr, Owens, Grant, Walton, Owens & Wallace 1995, Journal of Endocrinology 145, 545–557; Kind, Owens, Robinson, Quinn, Grant, Walton, Gilmour & Owens 1995, Journal of Endocrinology 146, 23–34).

The fixed and additional random effects included in the model for statistical analysis of IGF-I, IGF-II, IGFBP-3 and animal production and carcass traits are presented in Table 5. The fixed effects used for statistical analysis of reproduction traits are presented in Table 6.

Linear covariables included exact age in days for ANW21, animal weight at 18 weeks of age for DFI, animal weight at 23 weeks of age for P2, and animal weight at recording for LEAN.

Following preliminary analyses that showed there were no significant genetic correlations between ANW21 and IGF-I, IGF-II or IGFBP-3, ANW21 was included as a linear covariate in analyses for these traits.

Heritabilities for and correlations between IGF-I, IGF-II and IGFBP-3 and production and/or carcass and/or reproduction traits were obtained from a series of bivariate analysis using DFREML, a computer software program designed for estimation of variance (Madsen, P., Jensen, J.

and Thompson, R., 1994, Estimation of (co)variance components by REML in multivariate mixed linear models using average of observed and expected information, 5th World Congress of Genetics Applied to Livestock Production, Volume 22, pages 19–22).

TABLE 5

Fixed and additional random effects used in the analysis of IGF-I, IGF-II, IGFBP-3 and animal production and carcass traits.

| TRAIT | breed | wkaba | wkca | parity | yearwk | recdate |
|---|---|---|---|---|---|---|
| IGF-I# | yes | yes | no | yes | no | no |
| IGF-II# | yes | yes | no | yes | no | no |
| IGFBP-3# | yes | no | yes | yes | no | no |
| ANW21# | yes | no | no | yes | yes | no |
| ADG# | yes | no | no | yes | no | yes |
| P2 | yes | no | no | no | no | yes |
| DFI | yes | no | no | no | no | yes |
| DFE | yes | no | no | no | no | yes |
| LEAN | yes | no | no | no | no | yes |

\#, litter code included as an additional random effect
breed = large white, landrace or duroc
wkaba = IGF assay batch
wkca = IGFBP-3 assay batch
parity = sow parity (ie. whether this was her first, second, third or fourth pregnancy)
yearwk = week and year of birth
recdate = date the trait was recorded

TABLE 6

Fixed effects used in the analysis for reproduction traits

| TRAIT | breed | fseas1 | fseas2 | fseas3 | AI1 | modfa2 | modfa3 |
|---|---|---|---|---|---|---|---|
| $NBA_1$ | yes | yes | no | no | yes | no | no |
| $NBA_2$ | yes | no | yes | no | no | yes | no |
| $NBA_3$ | yes | no | no | yes | no | no | yes | breed = sow breed
fseas = farrowing (pregnancy) year or season code for the appropriate farrowing
AI1 = AI or natural mating code for the first litter
modfa = farrowing module (location) for the appropriate parity Results Table 7 summarises the number of observations of each trait.

Heritability estimates and variance components of those estimates for IGF-I, IGF-II, IGFBP-3 and common litter effects are presented in Table 8.

The estimated heritabilities for IGF-I and IGFBP-3 obtained in this example (Table 8) are consistent with those obtained in Example 1 (Table 2). There are differences due, in part, to the larger number of observations obtained in the second example.

Genetic correlations between traits analysed are presented in Tables 9 and 11.

TABLE 7

Number of observations (N) for different traits

| TRAIT | N |
|---|---|
| IGF-I | 1,551 |
| IGF-II | 1,551 |
| IGFBP-3 | 1,542 |
| Number born alive per mating - for first pregnancy | 5,966 |
| Number born alive per mating - for second pregnancy | 4,097 |
| Number born alive per mating - for third pregnancy | 2,952 |
| Liveweight at 3 weeks | 4,670 |
| Average growth rate (birth to 23 weeks) | 3,522 |
| Finisher feed intake (17 to 23 weeks) | 3,531 |
| Finisher feed efficiency (feed/gain, 17 to 23 weeks) | 3,500 |
| Carcass lean | 2,318 |
| Carcass backfat (P2) | 3,575 |

TABLE 8

Estimates of heritabilities ($h^2$, ±SEM) and common litter effects ($c^2$, ±SEM) along with additive ($\sigma_a$), litter ($\sigma_l$), environmental ($\sigma_e$) and phenotypic variances ($\sigma_p$).

| TRAIT | $h^2$ | $c^2$ | $\sigma_a$ | $\sigma_l$ | $\sigma_e$ | $\sigma_p$ |
|---|---|---|---|---|---|---|
| IGF-I | 0.22 ± 0.09 | 0.19 ± 0.05 | 137.1 | 116.8 | 360.5 | 614.4 |
| IGF-II | 0.18 ± 0.08 | 0.18 ± 0.04 | 275.8 | 264.5 | 962.7 | 1503 |
| IGFBP-3 | 0.19 ± 0.08 | 0.18 ± 0.05 | $7.7 \times 10^{-3}$ | $7.4 \times 10^{-3}$ | $25.1 \times 10^{-3}$ | $40.1 \times 10^{-3}$ |

TABLE 9

Genetic correlations (±SEM) between blood plasma concentrations of insulin-like growth factors I and II, insulin-like growth factor-binding protein-3, growth performance and carcass characteristics.

| TRAIT | IGF-I | IGF-II | IGFBP-3 |
|---|---|---|---|
| IGF-II | +0.21 ± 0.44 | | |
| IGFBP-3 | +0.84 ± 0.37 | +0.40 ± 0.47 | |
| Growth rate | −0.47 ± 0.38 | +0.04 ± 0.35 | −0.28 ± 0.37 |
| Feed intake | +0.37 ± 0.31 | +0.16 ± 0.33 | +0.26 ± 0.33 |
| Feed efficiency (feed/gain) | +0.84 ± 0.48 | +0.37 ± 0.46 | +0.61 ± 0.47 |
| Carcass backfat (P2) | +0.29 ± 0.23 | −0.02 ± 0.24 | +0.16 ± 0.24 |
| Carcass lean | −0.26 ± 0.26 | +0.03 ± 0.28 | −0.20 ± 0.28 |

A large positive genetic correlation between IGF-I and IGFBP-3 was apparent in this example (Table 9) and in the previous example (Table 3), suggesting that traits IGF-I and IGFBP-3 are controlled by some common genes. Genetic correlations between IGF-II and IGF-I or IGFBP-3 were low to moderate in magnitude indicating that IGF-II is controlled largely by a different set of genes. IGF-II may therefore be considered as a different trait.

Genetic correlations between IGF-I or IGFBP-3 and growth rate or carcass lean were negative and moderate in magnitude (Table 9). Genetic selection for low levels of IGF-I and/or IGFBP-3 in prepubertal animals will therefore increase growth rate and carcass lean of their progeny. In a preliminary experiment using a much smaller number of animals, growth rate was observed to be positively genetically correlated with IGFBP-3. In the current example, however, the genetic correlation between IGFBP-3 and growth rate was negative and is biologically consistent with the genetic correlations observed in this example between IGFBP-3 and feed efficiency (feed/gain), carcass lean and P2 backfat.

For carcass backfat (P2), feed intake and feed efficiency (expressed here as feed intake divided by liveweight gain or feed/gain), the genetic correlations with IGF-I, IGF-II or IGFBP-3 were generally positive and high in magnitude. The very high genetic correlations between IGF-I or IGFBP-3 and feed efficiency (feed/gain) reflect the opposing signs of the correlations between IGF-I or IGF-II and/or IGFBP-3 with feed intake and growth rate. Genetic selection for low levels of IGF-I, IGF-II and/or IGFBP-3 in prepubertal animals will therefore decrease carcass backfat, reduce feed consumption and improve feed efficiency (ie. reduce the ratio of feed/gain) of their progeny.

The large positive genetic correlation observed between IGF-I and IGFBP-3 is not unexpected. A considerable body of previous literature shows that growth hormone (also known as somatotropin), a natural product of pigs and other vertebrates, increases synthesis and secretion into blood of both IGF-I and IGFBP-3. There is also a large body of published literature showing that IGF-binding proteins, particularly IGFBP-3, reduce the clearance of IGF-I from blood. Furthermore, most of the insulin-like growth factors in blood are present in complexes formed by association with IGF-binding proteins, including IGFBP-3.

The results show that selection of replacement breedstock for low IGF-I and/or IGF-II and/or IGFBP-3 during prepubertal life will result in decreased feed intake of the population in the next generation of animals. Such selection will also increase feed efficiency (ie. reduce the feed to gain ratio).

Also consistent with the above results, genetically selecting for low IGF-I and/or IGFBP-3 in the population will reduce carcass backfat (P2) because of the positive genetic correlations observed between these traits. Similarly, decreasing IGF-I and/or IGFBP-3 in the breeding population will increase lean content in the carcasses of their progeny, because of the negative genetic correlations between these traits.

The above pattern of genetic correlations are physiologically consistent with each other.

The negative genetic correlation between IGF-I and carcass backfat is the opposite of that predicted, because IGF-I administration is reported to reduce fatness in animals (Tomas et al., 1993).

Genetic correlations between IGF-I and feed efficiency, expressed here as weight of feed consumed divided by live weight gained, have not been previously reported. The positive sign of this correlation is the opposite of that expected from understanding the prior art because administration of IGF-I to animals has been reported to reduce their feed/gain ratio (Tomas et al., 1993).

Genetic correlations between IGFBP-3 and other biological traits have not been reported previously.

Overall phenotypic correlations are presented in Table 10. As observed in the first example, the genetic correlations between insulin-like growth factors and growth performance or carcass quality were stronger than the phenotypic correlations between these traits. Genetic correlations between IGF-I, IGF-II or IGFBP-3 and reproductive performance, measured as the number of animals born alive from each mating, are presented in Table 11.

TABLE 10

Phenotypic correlations between blood plasma concentrations of insulin-like growth factors I and II, insulin-like growth factor-binding protein-3, growth performance and carcass characteristics.

| TRAIT | IGF-I | IGF-II | IGFBP-3 |
|---|---|---|---|
| IGF-II | +0.57 | | |
| IGFBP-3 | +0.79 | +0.67 | |
| Growth rate | +0.10 | +0.11 | +0.05 |
| Feed intake | +0.09 | +0.02 | +0.10 |
| Feed efficiency (feed/gain) | +0.05 | +0.04 | +0.06 |
| Carcass backfat (P2) | +0.19 | +0.08 | +0.16 |
| Carcass lean | −0.18 | −0.04 | −0.16 |

As the traits of IGF-I, IGF-II and IGFBP-3 were measured on a different group of animals to those measured for the trait number born alive (Table 7), environmental covariances between these traits are zero. In this analysis it is therefore not possible to estimate either environmental or phenotypic correlations between IGF-I, IGF-II or IGFBP-3 and number born alive.

Genetic correlations between IGF-I, IGF-II or IGFBP-3 and number born alive in first pregnancies (parity one) were consistently negative and low to moderate in magnitude. In contrast, genetic correlations with second (parity two) and third pregnancies (parity three) were generally positive and moderate to high in magnitude.

TABLE 11

Genetic correlations between blood plasma concentrations of insulin-like growth factors I and II, insulin-like growth factor-binding protein-3, and number of animals born alive

| | Number of Animals Born Alive in the | | |
|---|---|---|---|
| TRAIT | First Pregnancy | Second Pregnancy | Third Pregnancy |
| IGF-I | −0.28 | +0.25 | +0.51 |
| IGF-II | −0.49 | −0.03 | +0.73 |
| IGFBP-3 | −0.14 | +0.26 | +0.76 |

These results indicate that genetic selection to reduce IGF-I, IGF-II or IGFBP-3 will have favourable consequences for number of animals born alive in first pregnancies, but will have unfavourable consequences for number born alive in later pregnancies.

The pattern of genetic correlations observed above may be the result of several factors. These include the apparent change in physiological status of dams between first and subsequent pregnancies as a result of reduced demands to meet requirements for growth compared to requirements for reproduction.

Finally, it is understood that various other modifications and/or alterations may be made without departing from the spirit of the present invention as outlined herein.

What is claimed is:

1. A method for identifying an animal within a specific breed or line that is subsequently likely to produce offspring with higher than average carcass quality, better than average feed conversion efficiency, higher than average growth rate, lower than average voluntary feed intake or higher than average reproductive capacity, where the average is determined in animals of the same age and within the same line, which method includes determining the concentration of insulin-like growth factor-I (IGF-I), insulin-like growth factor-II (IGF-II) or insulin-like growth factor binding protein-3 (IGFBP-3) by measurement in a comparable biological sample from said animals taken at any time between birth and the onset of puberty, and selecting for breeding those animals in which said concentration is lower than the average for animals within the same line and of the same age, wherein said animal is a livestock member.

2. A method according to claim 1 wherein the biological sample is blood, serum or plasma.

3. A method according to claim 2 wherein the concentration of IGF-I, IGF-II, or IGFBP-3 is measured by a radioimmunoassay, an immunoradiometric assay, or an enzyme-linked immunochemical assay.

4. A method according to claim 1, wherein said livestock is selected from the group consisting of pigs, sheep, cattle, goats, deer, horses, rabbits, fish and birds.

5. A method according to claim 4 wherein th animals are pigs.

* * * * *

UNITED STATES PATENT AND TRADEMARK OFFICE
CERTIFICATE OF CORRECTION

PATENT NO. : 6,090,569
DATED : July 18, 2000
INVENTOR(S) : Phillip Clyde Owens, et al.

It is certified that error appears in the above-identified patent and that said Letters Patent is hereby corrected as shown below:

On title page, item 73, "South Africa" should read - - Australia - -.

Signed and Sealed this

Fifteenth Day of May, 2001

Attest:

NICHOLAS P. GODICI

Attesting Officer     Acting Director of the United States Patent and Trademark Office